United States Patent [19]
Koike et al.

[11] Patent Number: 5,716,367
[45] Date of Patent: Feb. 10, 1998

[54] CATHETER ASSEMBLY FOR INTRACARDIAC SUTURE

[75] Inventors: Kazuyuki Koike, Tokyo-to; Yoshikazu Kishigami, Ohtsu; Katsuya Miyagawa, Shiga-ken; Nozomu Fujita, Ohtsu, all of Japan

[73] Assignee: Nissho Corporation, Osaka-fu, Japan

[21] Appl. No.: 731,748

[22] Filed: Oct. 18, 1996

[30] Foreign Application Priority Data

Oct. 18, 1995 [JP] Japan ................. 7-269916

[51] Int. Cl.$^6$ ................................ A61B 17/00
[52] U.S. Cl. ................ 606/144; 606/139; 606/213
[58] Field of Search ............................. 606/139, 140, 606/141, 144; 604/36, 40, 93

[56] References Cited

U.S. PATENT DOCUMENTS

| | | | |
|---|---|---|---|
| 4,085,743 | 4/1978 | Yoon | 606/140 |
| 5,281,234 | 1/1994 | Wilk et al. | 606/139 |
| 5,431,639 | 7/1995 | Shaw | 606/213 |
| 5,536,242 | 7/1996 | Willard et al. | 604/40 |

FOREIGN PATENT DOCUMENTS 5-237128  9/1993  Japan.

*Primary Examiner*—Gary Jackson
*Attorney, Agent, or Firm*—Birch, Stewart, Kolasch & Birch, LLP

[57] ABSTRACT

A catheter assembly for intracardiac suture comprises a hooking catheter (4) provided at a distal end with a suture-hooking member (42) and at the proximal end with a manipulating element (41) at a proximal end thereof; a first sheath (3) for movably holding the hooking catheter therein; a piercing catheter (2) for movably holding the first sheath, provided at a distal end with a piercing needle and at the proximal end with a hemostatic valve 29; and a second sheath (1) for movably holding the piercing catheter, provided at the proximal end with a hemostatic valve 19. The piercing catheter (2) and second sheath (1) are provided at each distal portion with a side hole (21, 11) so that the side hole (21) of the piercing catheter (2) is laid to lie the side hole (11) of the second sheath (1) when the tip of the piercing catheter (2) is reached to the tip of the second sheath to allow the first sheath (3) to protrude through the overlapped side holes (21, 11).

5 Claims, 17 Drawing Sheets

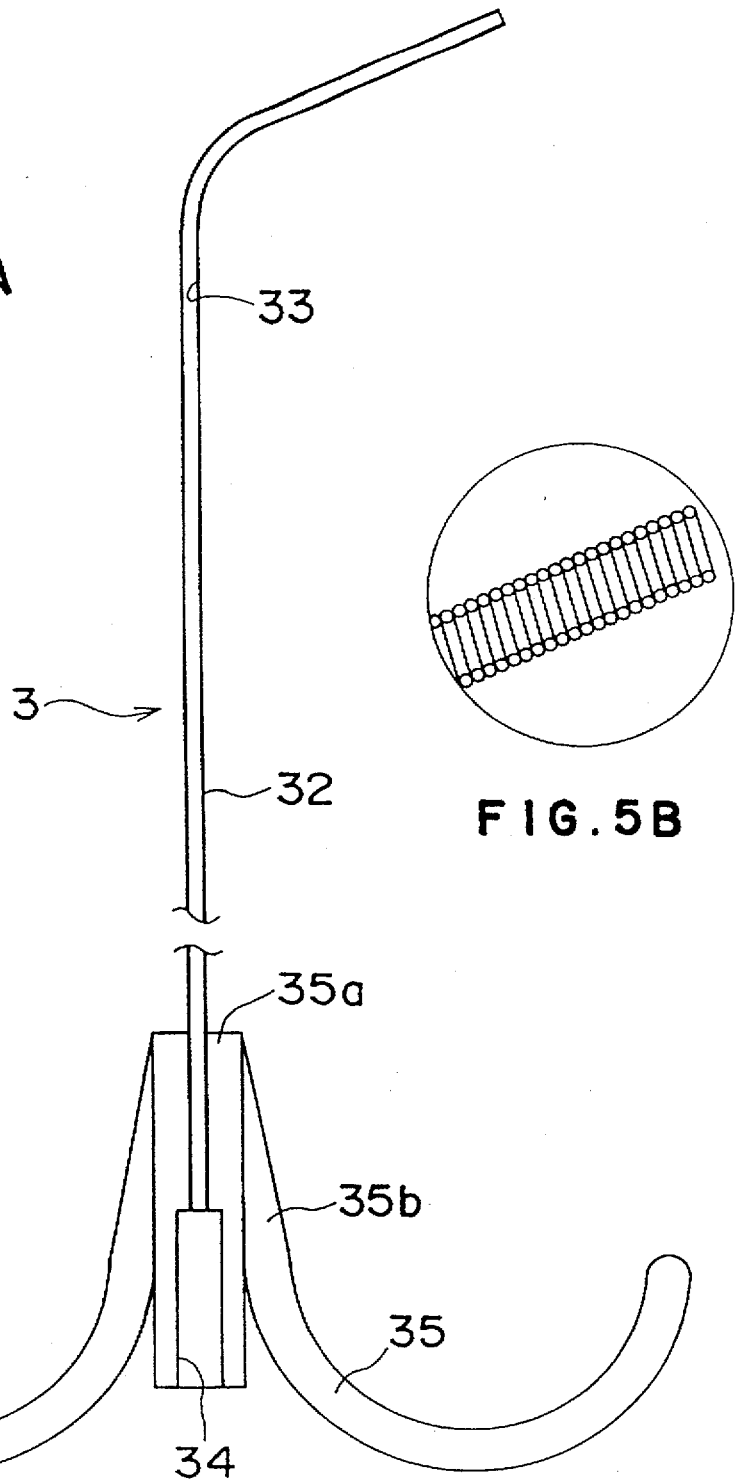

CATHETER ASSEMBLY FOR INTRACARDIAC SUTURE

FIELD OF THE INVENTION

The present invention relates to a catheter assembly for intracardiac suture and, more particularly, to a catheter assembly for intracardiac suture procedure suitable for surgical technique, so-called transcatheter atrioseptopexy, in which a sewing device is inserted into a peripheral blood vessel and manipulated into the heart by cardiocatheterization under cross-sectional echocardiography to sew an atrial septal defect (ASD) by direct suturing.

BACKGROUND OF THE INVENTION

A surgical procedure for occlusion of atrial septal defects, known as a percutaneous transluminal therapeutic catheterization, is carried out by transvascularly inserting a cardiocatheter into the heart and the first clinical success has been reported in 1976 by King and Mill. In this procedure, an atrial septal defect is closed by introducing a pair of umbrella-like members into the atrium with an insertion tool composed of a double-layered catheter and a core wire arranged therein, placing said members on opposite sides of the defect, and locking them together at a central hub which crosses the defect.

However, this method requires use of a very large-sized insertion tool and hard umbrella-like members, thus making it impossible to apply it to children, especially, to preschool children. For this reason, as a result of efforts to miniaturize such a device, Rashkind developed a plug of single umbrella type having a hook and succeeded in clinical application to a child in 1977. However, this method has a such defect that the plug is hooked on an unintended site of the heart because of being provided with the hook. Once the umbrella-like member is opened, it is impossible to change its hooked position as well as to draw back the device from the heart. This requires emergent surgical operation when the plug is hooked on an unintended site of the heart. In order to overcome such a disadvantage, Rashkind has further developed a plug comprising two umbrella-shaped occuluders having eight stainless struts and being connectable to each other. This device is now put into clinical use widely to occlusion of patent ductus arteriosus.

Japanese unexamined patent application No. 5-237128 filed by James E. Lock et al discloses an interatrial occlusion device comprising two umbrella-shaped members composed of eight stainless steeltruts like as the Rashkind's device, each strut being provided at a central part thereof with a spring coil. This device is firmly fixed to the thin interatrial septum by closely adhering two umbrella-shaped members to each other in the overlapping state. This device is called as a clam shell-shaped interatrial occluder because of its configuration similar to that of a clam being a bivalve. The procedure is carried out by inserting an elongated sheath with a thickness of 11 French through the femoral vein. This device has been widely used for closing atrial septal defects by means of percutaneous transluminal therapeutic catheterization since the device can be applied to patients with a weight of 8 Kg and above.

However, there is a limited to the application of these devices. Since these devices need use of the occlusion plugs with a uniform shape for various configurations of atrial septal defects and since the occlusion of a defective opening or hole requires use of an occlusion plug twice the size of the defective opening or hole, these devices can be applied only to a relatively small defective openings or holes present in the central part of the atrioventricular septum. In addition, there is a fear of evil effects due to use of occlusion plugs since there is no data on long-term use of the occlusion plug left in the heart.

SUMMARY OF THE INVENTION

It is therefore an object of the present invention to provide a catheter assembly for intracardiac suture procedure suitable for application to atrial septal defect (ASD) with various configurations.

According to the present invention, the above object is achieved by providing a catheter assembly for intracardiac suture, comprising:

a hooking catheter bent at a distal portion thereof and having suture-hooking means at a distal end thereof and a manipulating element at a proximal end thereof;

a first sheath having a lumen for movably holding said hooking catheter therein, said first catheter being bent at a distal portion thereof at the same angle as the hooking catheter;

a piercing catheter having a lumen for movably holding said first sheath, said piercing catheter being provided at a distal end with a piercing needle and at the proximal end with a hemostatic means; and a second sheath having a lumen for movably holding said piercing catheter, said second sheath being provided with a hemostatic means at a proximal end thereof, said piercing catheter and second sheath being provided at each distal portion thereof with a side hole for extrusion of said first sheath so that said side hole of said piercing catheter is laid to lie the side hole of said second sheath to allow the first sheath to protrude therethrough when the piercing catheter is inserted into the second sheath until the tip of the piercing needle has reached to the tip of the second sheath.

The piercing catheter and the second sheath may be bent at a distal portion beyond the side hole at the same angle to form it into an elbow-shaped bend. Preferably, the suture-hooking means includes two or more suture-hooking members each of which is formed into an L-shaped hook by bending a superelastic metal wire at the distal end thereof. The suture-hooking members are bundled at their proximal ends, extended outwardly therefrom, and then bent inwardly at the distal portion so that they do not intersect each other at the hooks. Generally, the distal portion of the suture-hooking means is bent at a bend angle of about 90 degrees, preferably, within the range of 80 to 100 degrees. The piercing catheter and the second sheath may be provided at respective proximal ends with a side injection channel for injecting heparinized physiological saline into the suturing site.

The above and other objects and features of the present invention will become clear from the following description taken in conjunction with the preferred embodiments thereof with reference to the accompanying drawings which are given by way of illustration only, and thus are not limitative of the present invention.

BRIEF DESCRIPTION OF THE DRAWINGS

FIG. 5 is a schematic view of a first sheath employed in the catheter assembly of FIG. 1;

DETAILED DESCRIPTION OF THE PREFERRED EMBODIMENTS

Figure 1:
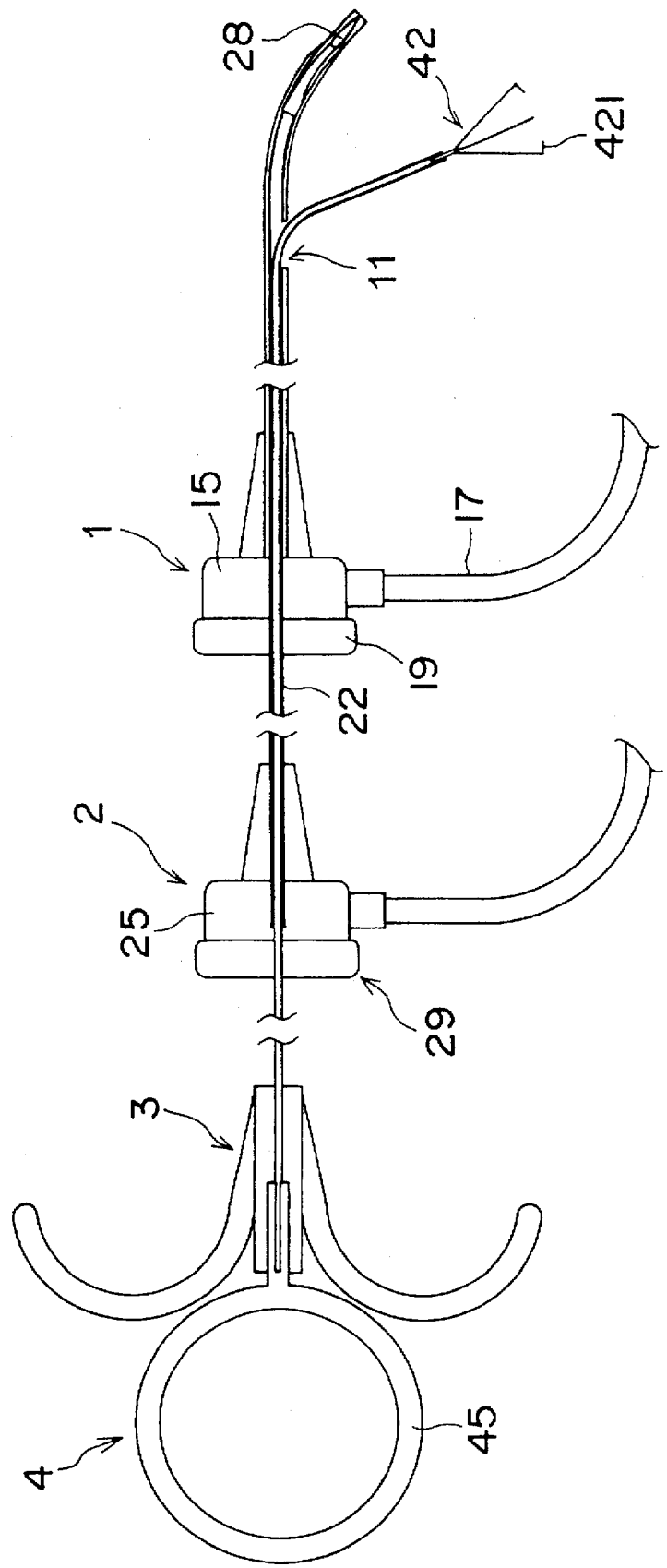
FIG. 1 is a schematic view of a catheter assembly for intracardiac suture according to the present invention.
Figure 2:
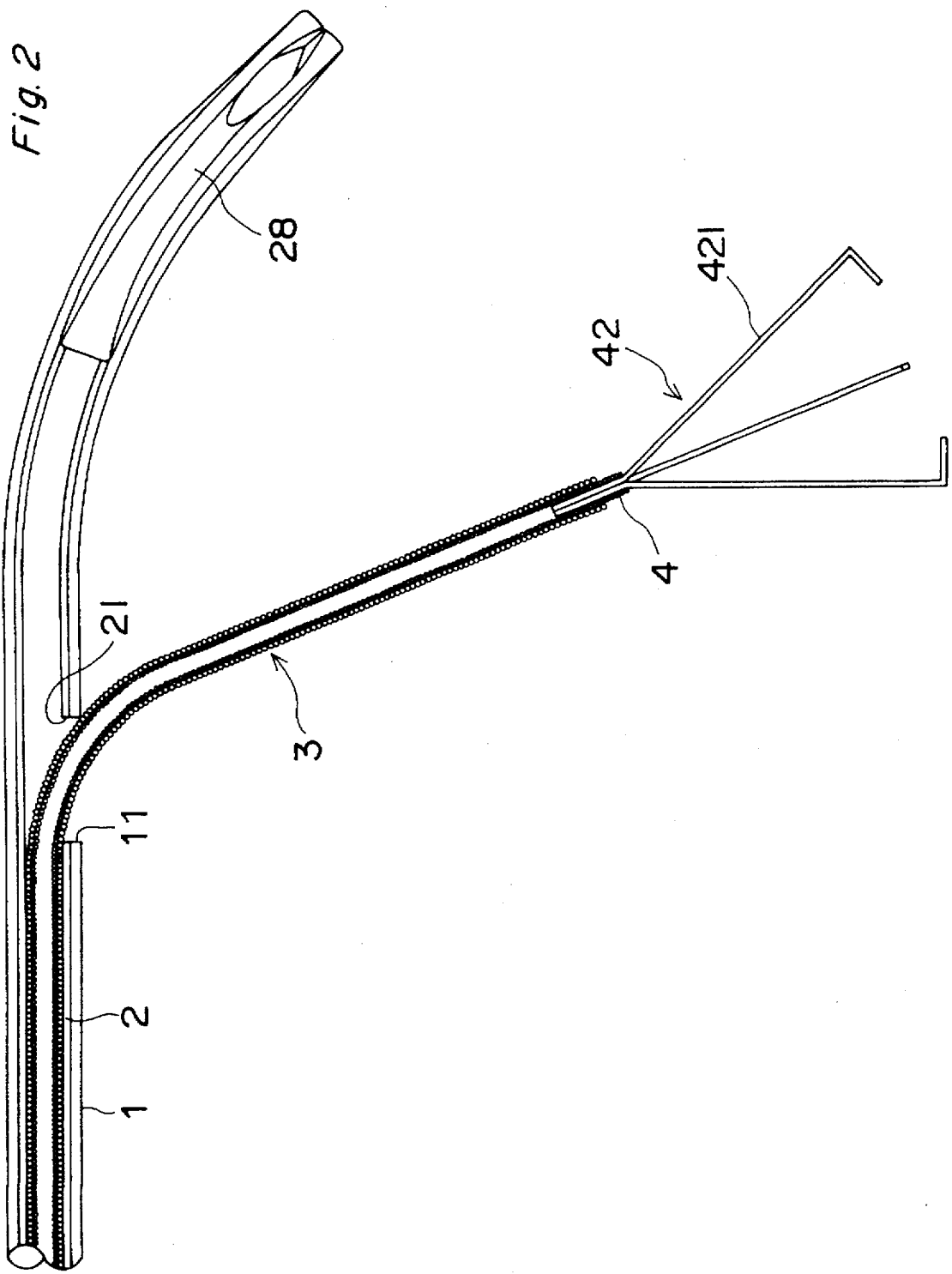
FIG. 2 is a enlarged sectional view of a tip of the catheter assembly of FIG. 1.

Referring now to FIGS. 1 to 6, there is shown a catheter assembly for intracardiac suture according to the present invention, comprising:

- a hooking catheter 4 bent at a distal portion thereof and having suture-hooking means 42 at a distal end thereof and a grip or manipulating element 45 at a proximal end thereof;
- a first sheath 3 having a lumen 33 for movably holding said hooking catheter 4 therein, said first catheter being bent at a distal portion thereof at the same angle as the hooking catheter 4;
- a piercing catheter 2 having a lumen 23 for movably holding said first sheath 3, said piercing catheter being provided at a distal end with a piercing needle 28 and at the proximal end with a hemostatic means 29; and
- a second sheath 1 having a lumen 13 for movably holding said piercing catheter 2, said second sheath being provided with a hemostatic means 19 at a proximal end thereof, said piercing catheter 2 and second sheath 1 being provided at each distal portion thereof with a side hole 21 or 11 for extrusion of said first sheath so that said side hole 21 of said piercing catheter 2 is laid to lie the side hole 11 of said second sheath 2 to allow the first sheath 3 to protrude therethrough when the piercing catheter 2 is inserted into the second sheath 2 until the tip of the piercing needle 28 has reached to the tip of the second sheath 2.

Figure 3:
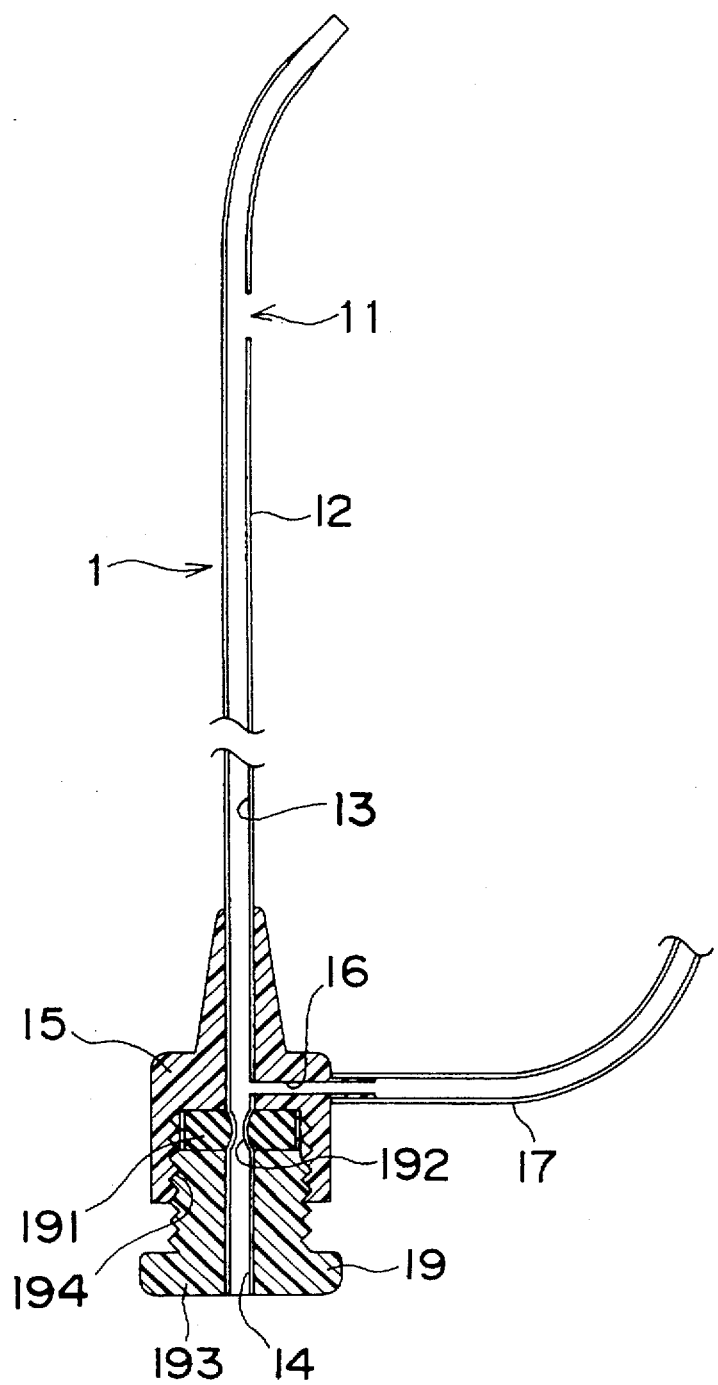
FIG. 3 is a schematic view of a second sheath employed in the catheter assembly of FIG. 1.

As best shown in FIG. 3, the second sheath 1 is composed of a sleeve 12 with a lumen 13 for free insertion of the piercing catheter 2. The sleeve 12 is provided at its proximal end with a connector 15 and on its distal end with a side hole 11 for passing the first sheath 3 through. The connector 15 has an inlet of lumen 13, i.e., an insertion hole 14 for the piercing catheter 2, and is provided with a hemostatic means or a hemostatic valve 19 to prevent leakage of the blood during surgical operation. The hemostatic valve 19 is not limited in construction.

In this embodiment, the hemostatic valve 19 is composed of a screw-hole or nut-like means 194 provided in a rear end of the connector 15, and a packing 191 with a central through-hole 192, and a bolt-like member 193 engaged with screw-hole 194, as shown in FIG. 3. By driving the bolt-like member 193 in, the packing 191 is pressed against the bottom wall of the screw-hole 194 to adjust an inner diameter of the through-hole 192. Further, the connector 15 is generally provided with a side injection channel 16 for injecting heparinized physiological saline into the site to prevent occurrence of blood coagulation during surgical operation, and the side injection channel 16 is connected to a side injection tube 17. Preferably, the distal portion of the sleeve 12 is curved in correspondence with the intracardiao shape of the patient, taking account of manipulatability. The curved angle of the distal portion is preferably set to about 30 degrees.

As a material for sleeve 12 of the second sheath 1, there may be used a mesh or coil of stainless steel (e.g., SUS 304), and synthetic resins such as fluororesin (e.g., polytetrafluoroethylene), polypropylene, polyethylene, polyamide, polyethylene terephthalate, polyurethane, and the like. A material for connector 15 is generally made of a synthetic resin such as polypropylene, acrylonitrile-butadiene-styrene copolymer (ABS), polyvinyl chloride, polyethylene, polyethylene terephthalate and the like; or a metal such as stainless steel, brass and the like.

The packing 191 may be made of a material with a rubber elasticity, for example, natural rubber or synthetic rubber such as silicone rubber, isoprene rubber, and the like. As a material for bolt-like means, there may be used synthetic resins such as polycarbonate, ABS resins or the like.

Figure 4:
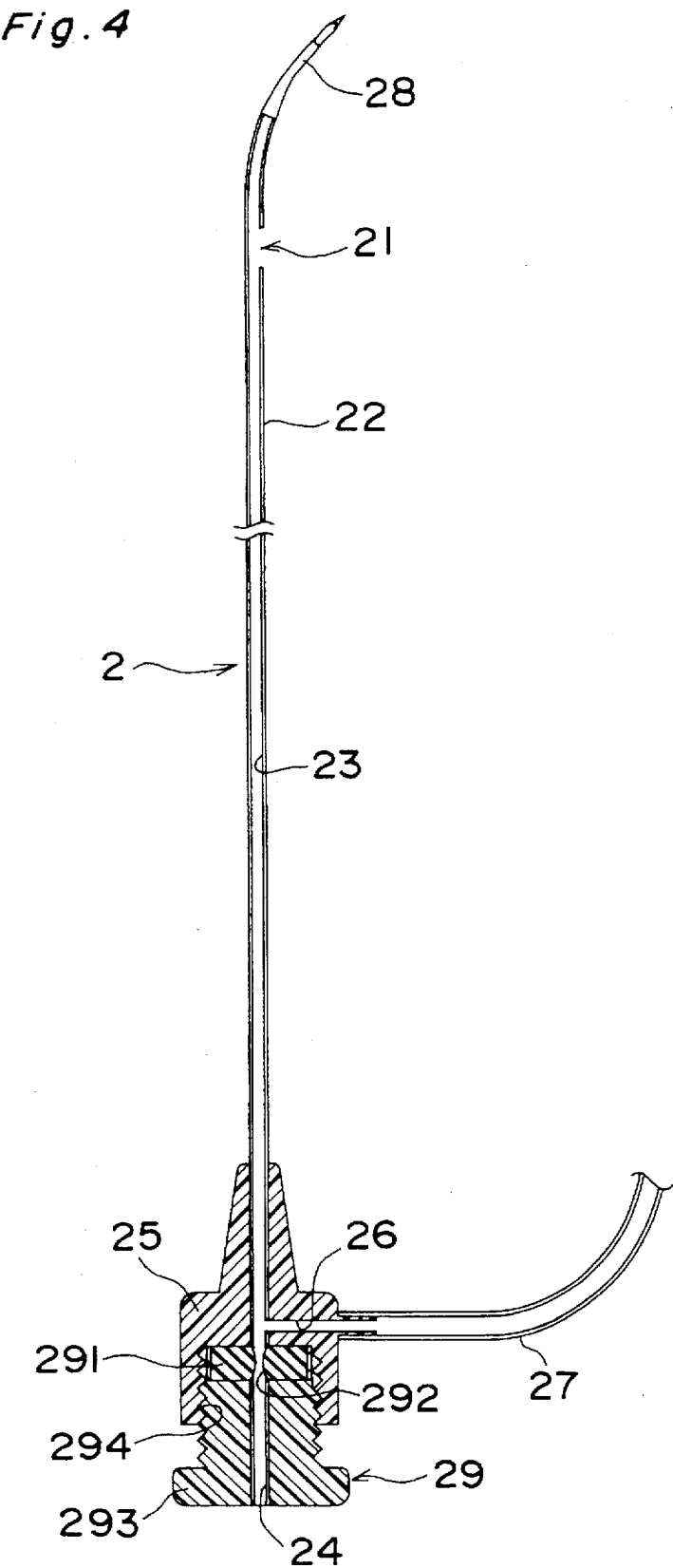
FIG. 4 is a schematic view of a piercing needle employed in the catheter assembly of FIG. 1.

As shown in FIG. 4, the piercing catheter 3 is composed of a slender tubular member or a sleeve 22 with two open ends. The sleeve 22 is provided at a distal end with a piercing needle 28 and at the proximal end with a connector 25. The sleeve 22 is provided with a side hole 21 at the distal end thereof for allowing the first sheath 3 to protrude from the lumen 23. The connector 25 is provided with an entrance to the lumen 23, i.e., a central bore 24 for insertion of the first sheath 3 and a hemostatic means(or a bleeding stop valve) 29 to prevent leakage of the blood during surgical operation. The hemostatic means 29 has the same structure as that of the valve 19 of the second sheath 1, and is composed of a packing 291, through-hole 292, a bolt-like member 293 and a nut member 294.

Further, the connector 25 is generally provided with a side injection channel 26 for injecting heparinized physiological saline into the site to prevent coagulation of the blood during surgical operation. The side injection channel 26 is connected to a side injection tube 27. Preferably, the distal portion of the sleeve 12 is formed in the shape of a curve bent in the same angle of that of the second sheath 1, taking account of manipulatability. When the piercing catheter 2 is inserted into the second sheath 1 until the tip of the piercing needle 28 is reached to the tip of the second sheath 1, the side hole 21 of the piercing catheter 2 is overlapped with the side hole 11 of the second sheath 1.

As a material for sleeve 22 of the piercing catheter 2, it is preferred to use a meshed or coiled stainless steeluch as SUS 304. The connector 25 is generally made of a synthetic resin such as polypropylene, ABS resin, polyvinyl chloride, polyethylene, polyethylene terephthalate or the like; or a metal such as stainless steel, brass or the like. The piercing needle 28 is generally made of stainless steel such as SUS 304.

As shown in FIG. 5, the first sheath 3 is composed of a sleeve 32 bent at a distal end thereof and provided at a proximal end thereof with a grip 35 for easy operations. The sleeve 32 is a coiled member produced by winding a wire of a metal such as stainless steel (e.g., SUS 304), tungsten, titanium or the like. The grip 35 is composed of a cylindrical body 35a and a pair of arms 35b extending outward therefrom and made of a suitable material such as a synthetic resin or a metal. There is no limited to a material for the grip 35. The body of the grip 35 is provided with a stepped central bore, i.e., a small sized portion and a large sized portion. The proximal end of the sleeve 32 is fitted in the small sized portion of the bore of the grip 35 so that a lumen 33 of the sleeve 32 opens into a large sized portion of the bore serving as an inlet 34 for the hooking catheter 4. The distal end of the sleeve 32 is generally bent at an angle of about 70 degrees to allow the first sheath 3 to go out of the sleeve 22 of the piercing catheter 2 with ease when the side hole 11 of the second sheath 1 and the side hole 21 of the piercing catheter 2 are overlapped.

Figures 6A, 6B:
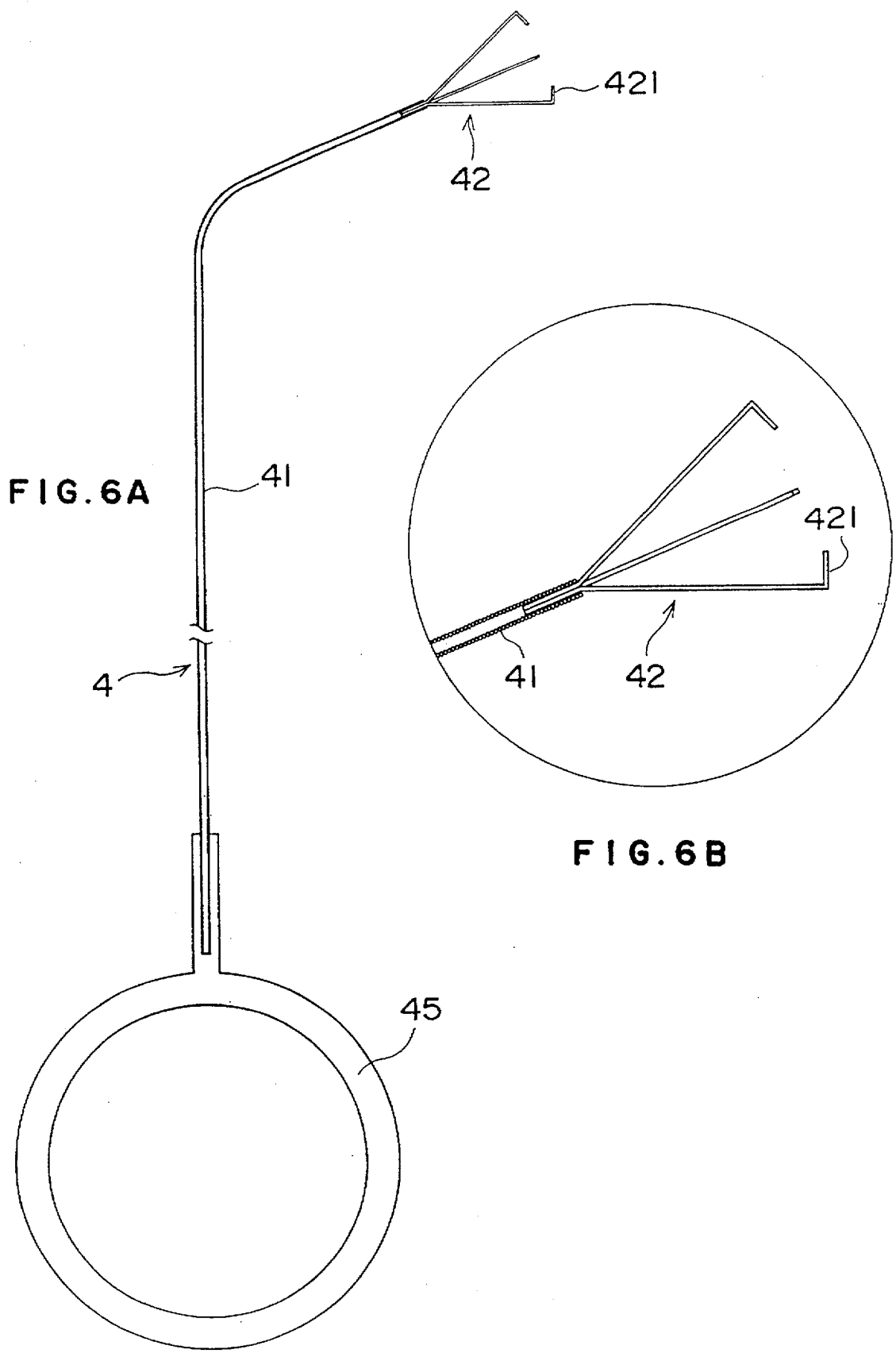
FIG. 6 is a schematic view of a hooking catheter employed in the catheter assembly of FIG. 1.

As best shown in FIG. 6, the hooking catheter 4 is composed of a shaft 41, suture-hooking means 42 fixed to a distal end of the shaft 41, and a finger ring 45 provided on a proximal end of the shaft 41 as a manipulating element. The shaft 41 is generally made of a metal wire wound into a continuous circular shape and bent at a distal portion thereof in the same manner as that of the first sheath 3. As a metal for the shaft 41, there may be used corrosion resisting materials such as stainless steel (e.g., SUS 304), tungsten, titanium and the like. The suture-hooking means 42 is generally composed of three or four hooking members which are generally made of metal wires of stainless steel (e.g., SUS 304), or a supper elastic metal (e.g., alloys of titanium-nickel, alloys including copper and zinc, or the like).

The hooking members are fixed at their proximal ends to the distal end of the shaft 41, extended outwardly and longitudinally from the shaft 41, and bent at their distal ends inwardly at an angle of about 90 degrees, preferably, in the range of 80 to 100 degrees to form an L-shaped hook 421. The proximal ends of the hooking members are so formed that the suture-hooking means 42 is able to expand outwardly at an angle of 15 to 30 degrees when it is stuck out of the first sheath 3. Because of such an arrangement, when the first sheath 3 is put out through the overlapped side holes 11, 21 of the second sheath 1 and the piercing catheter 2 and then the suture-hooking means 42 is stuck out of the first sheath 3, the hooking members does not intersect each other and can hold a suture at the hook 421.

The above parts are assembled into a catheter assembly as shown in FIG. 1 by inserting the piercing catheter 2 into the second sheath 1 so that the tip of piercing needle 28 is trued up with the tip of second sheath 2, inserting the first sheath 3 with the hooking catheter 4 into the piercing catheter 2 so that the first sheath 3 is put out through the side hole 21 of the piercing catheter 2 and the side hole 11 of the second sheath 1, and then pushing the hooking catheter 4 into the first sheath 3 so that the suture-hooking means 42 is expanded outwardly.

The suture hooking operations by hooking catheter 4 will be explained below, making reference to FIGS. 7 to 10.

Figure 7:
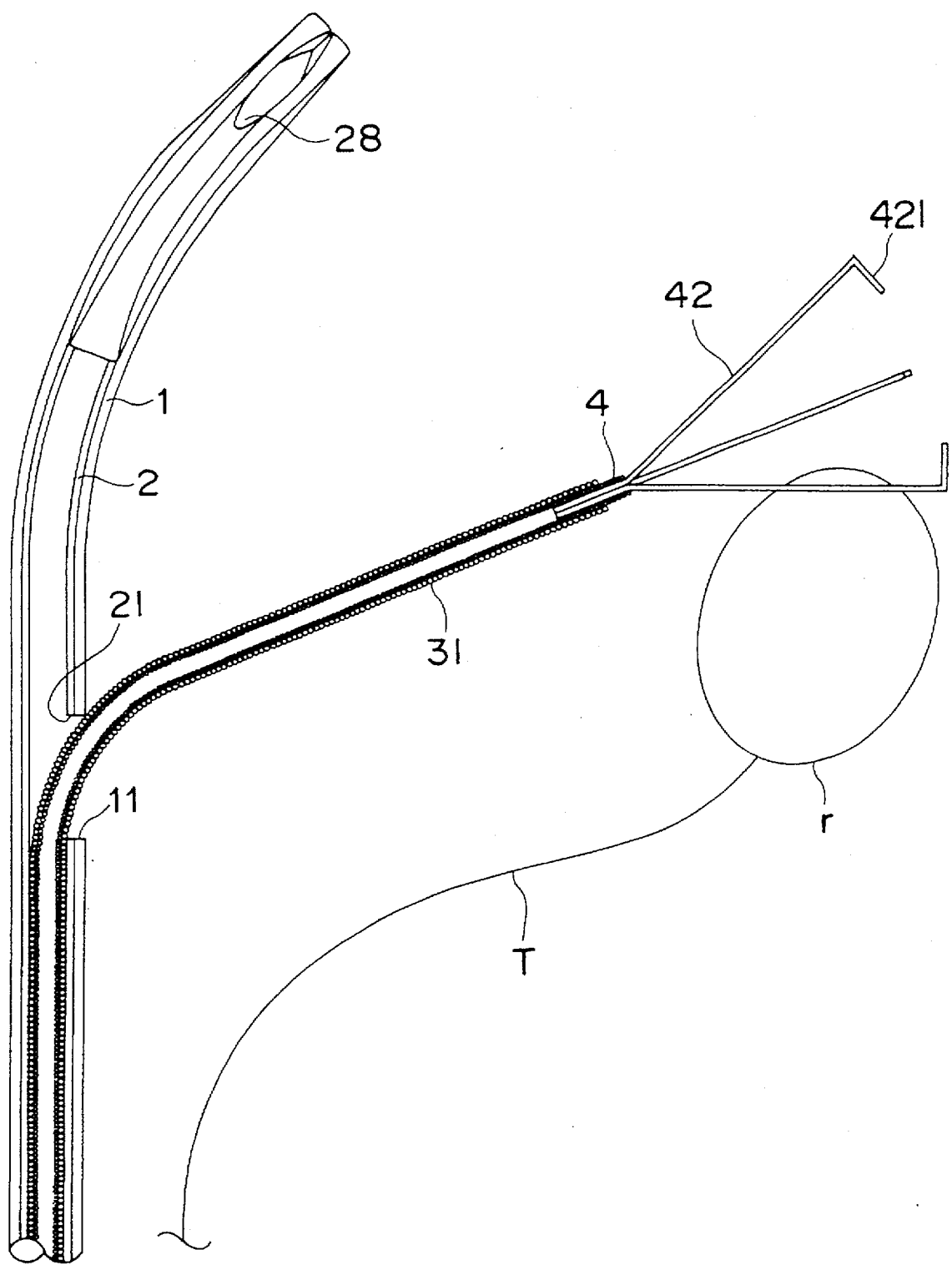
FIGS. 7 to 10 are schematic views illustrating operation for hooking a suture.
Figure 8:
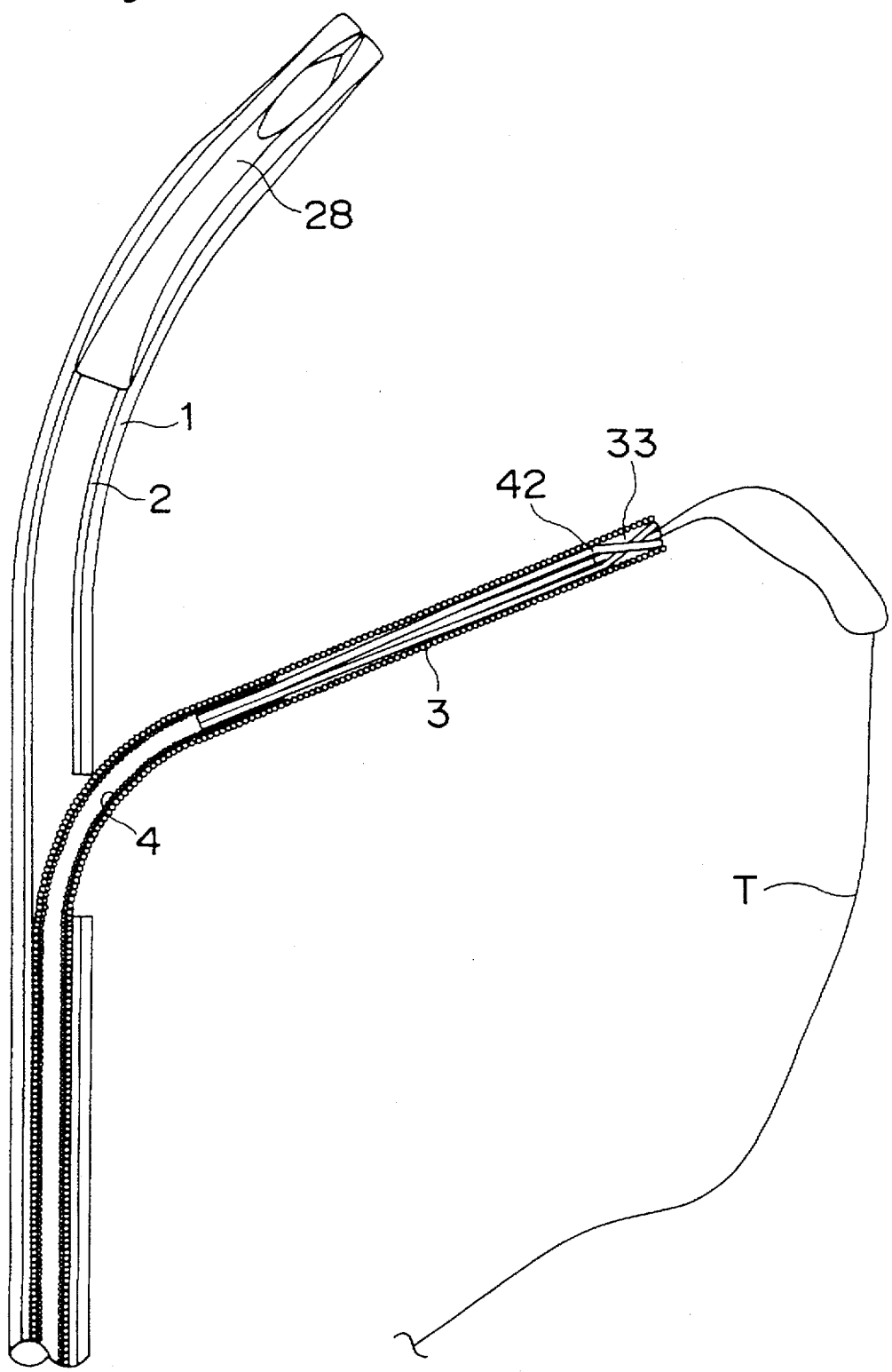

Firstly, a loop "r" of a suture T is hooked by the suture-hooking means 42 of the above catheter assembly as shown in FIG. 7. Then, the suture-hooking means 42 is drawn in the lumen 33 of the first sheath 3 as shown in FIG. 8 by pulling the operating ring 45 of the hooking catheter 4, while holding the first sheath 3 in the state of rest by the hand to avoid movement of the first sheath 3.

Figure 9:
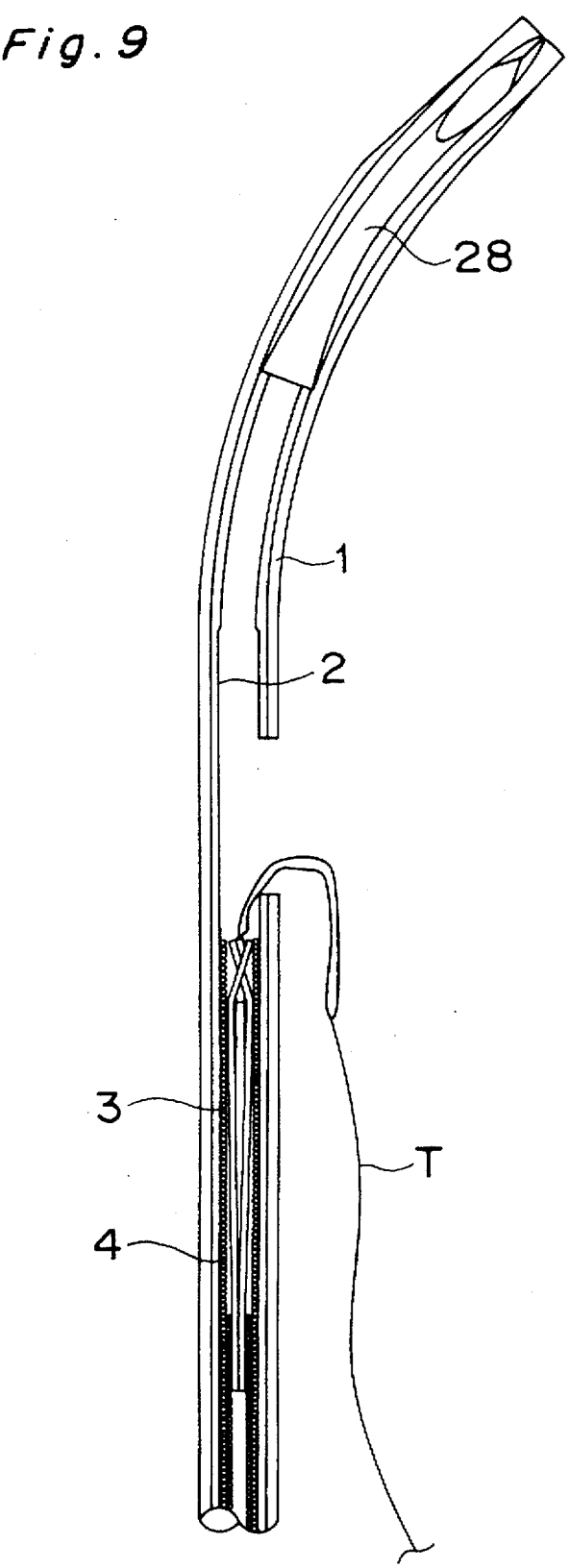
Figure 10:
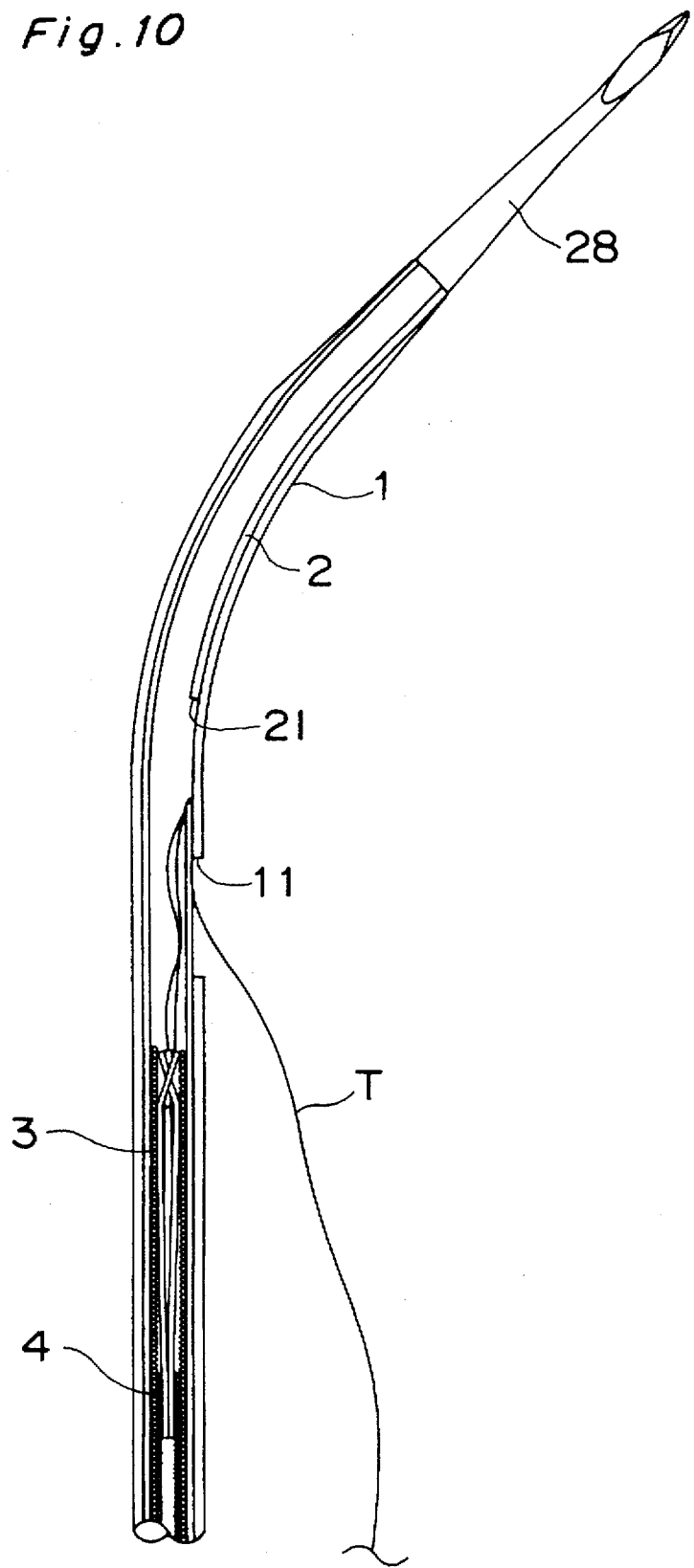

After the suture-hooking means 42 has been drawn in the lumen 33 of the first sheath 3, the first sheath 3 is pulled into the piercing catheter 2 together with the hooking catheter 4 as shown in FIG. 9 by pulling the grip 35 of the first sheath 3, while holding the piercing catheter 2 in the state of rest by the hand. Further, the first sheath 3 is pulled in the lumen of the piercing catheter 2 until the loop "r" of the suture T is hidden in the piercing catheter 2 as shown in FIG. 10.

Using the thus constructed catheter assembly for intracardiac suture according to the present invention, atrioseptopexy is carried out in the following manner. This atrioseptopexy will be explained below, making reference to the accompanying drawings of FIGS. 11 to 17.

Figure 16:
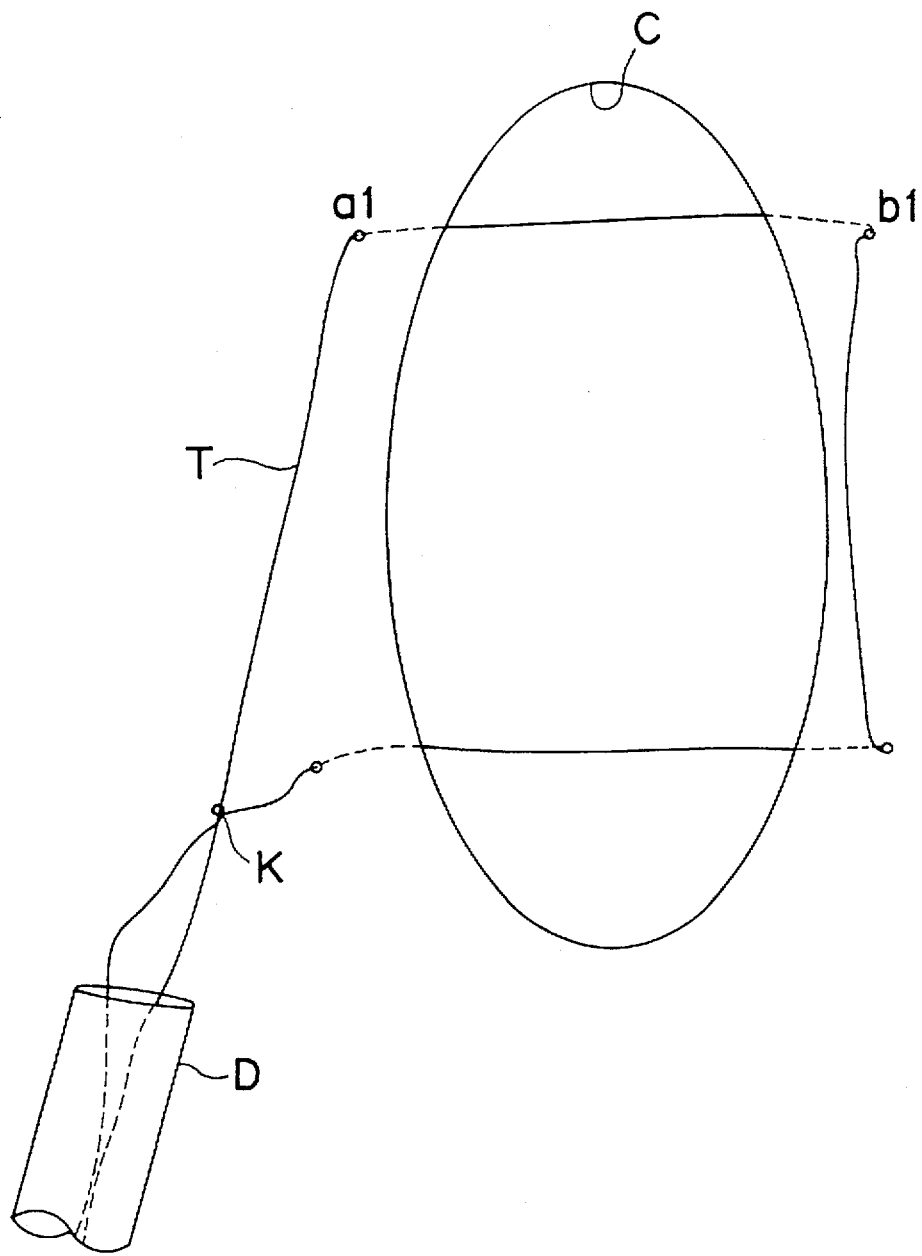

Firstly, the catheter assembly "A", which has been set in the state shown in FIG. 9, is inserted into a sheath "D" and maneuvered into the right atrium of a patient's heart through the sheath "D" (cf. FIG. 16). The sheath "D" has been maneuvered previously into the right atrium of a patient's heart through a femoral vein under observation of, via a mirror, a fluoroscoped image of the sheath as it traveled through the body of a patient. After the distal portion of the catheter assembly "A" has been reached to the interior of the right atrium, the piercing needle 28 is put out of the tip of the second sheath 1 as shown in FIG. 10 by pushing the connector 25 of the piercing catheter 2 forward by one hand, while holding the second sheath 1 in the state of rest by the other hand. In this condition, the side hole 11 of the second sheath 1 is off the side hole 21 of the piercing catheter 2. Thus, the suture T is put between the inner wall of the lumen 13 of the second sheath 1 and the outer wall of the piercing catheter 2 and thus held tightly.

Figure 11:
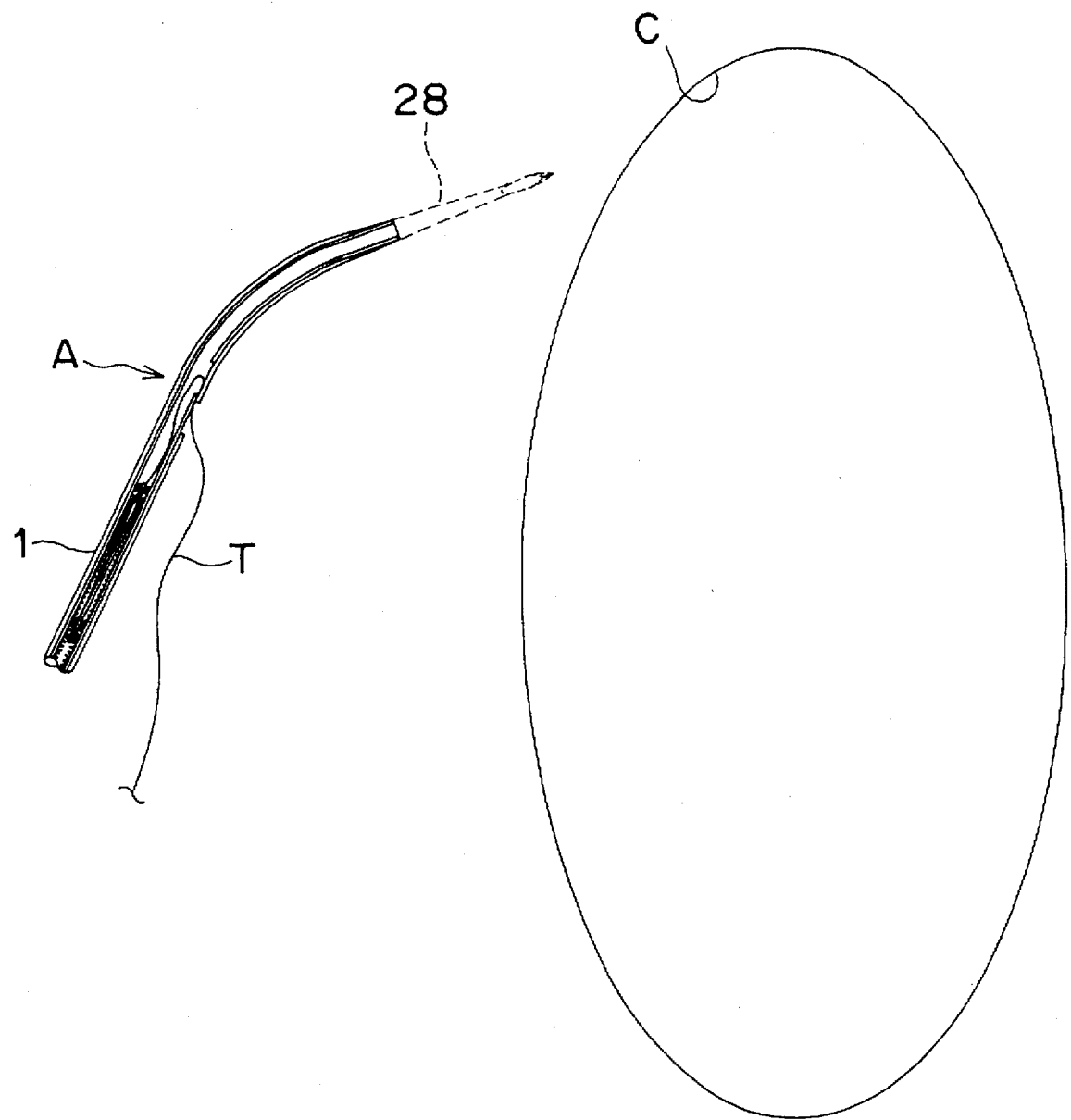
FIGS. 11 to 17 are explanatory views illustrating intracardiac suture with the catheter assembly of the present invention.

Then, the whole catheter assembly "A" is pushed to puncture the interatrial septum with the piercing needle 28 whereby the distal end of the catheter assembly "A" is inserted into the left atrium (FIG. 11). Next, the second sheath 1 is pushed to allow it to penetrate the interatrial septum, while holding the piercing catheter 2 in the state of rest by the hand. At the same time, the distal end of the piercing catheter 2 is drawn in the second sheath 1. In this state, the side hole 11 of the second sheath 1 is overlapped the side hole 21 of the piercing catheter 2. The catheter assembly "A" is further pushed into the left atrium until the overlapped side holes 11 and 21 are introduced into the left atrium. After this, the first sheath 3 is put into the left atrium through the side holes 11 and 21 by pushing the first sheath 3 while holding the piercing catheter 2 in the state of rest by the hand, and the loop "r" of the suture "T" is put out of the piercing catheter 2.

Figure 12:
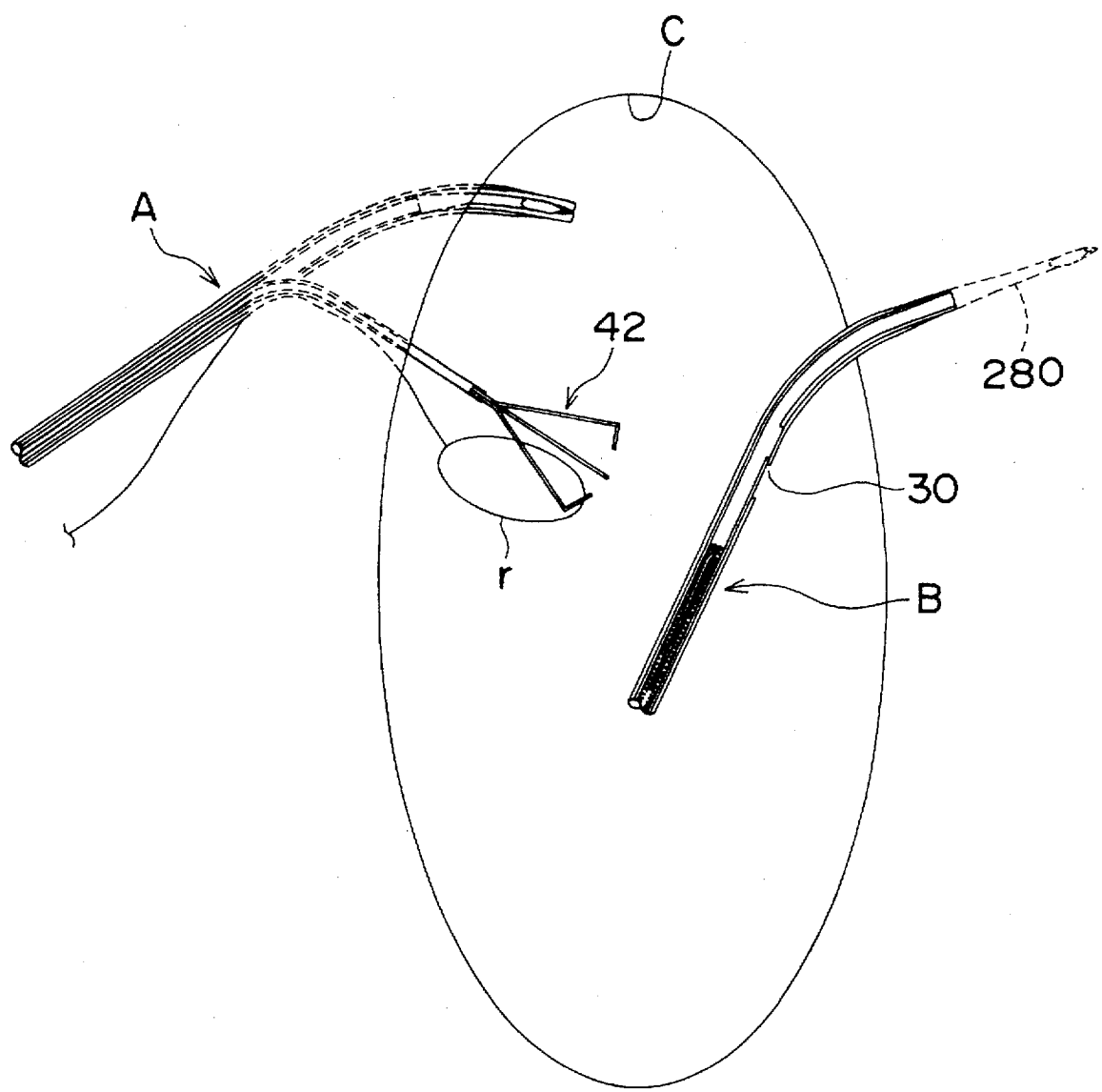

Separate from the above, another catheter assembly "B" with no suture, which has been set as shown in FIG. 9 with a suture being removed, is introduced into the right atrium of the patient's heart through a sheath (not shown) maneuvered previously into the right atrium through the femoral vein of the same or opposite side of the sheath "D". Then, the catheter assembly "B" is introduced into the left atrium, as shown in FIG. 12, through the interatrial septum from the opposite site to the insertion site of the catheter assembly "A" with respect to a defective aperture "C" in the same manner as that of the catheter assembly "A".

Then, the hooking catheter 40 is pushed, while holding the first sheath 30 of the assembly "B" in the rest state by the hand, whereby the distal end of the hooking catheter 40 is extruded from first catheter 30 and put in the left atrium. The suture "T" is caught by and transferred to the suture-hooking means 420 of the catheter assembly "B" from the suture-hooking means 42 of the catheter assembly "A".

Figure 13:
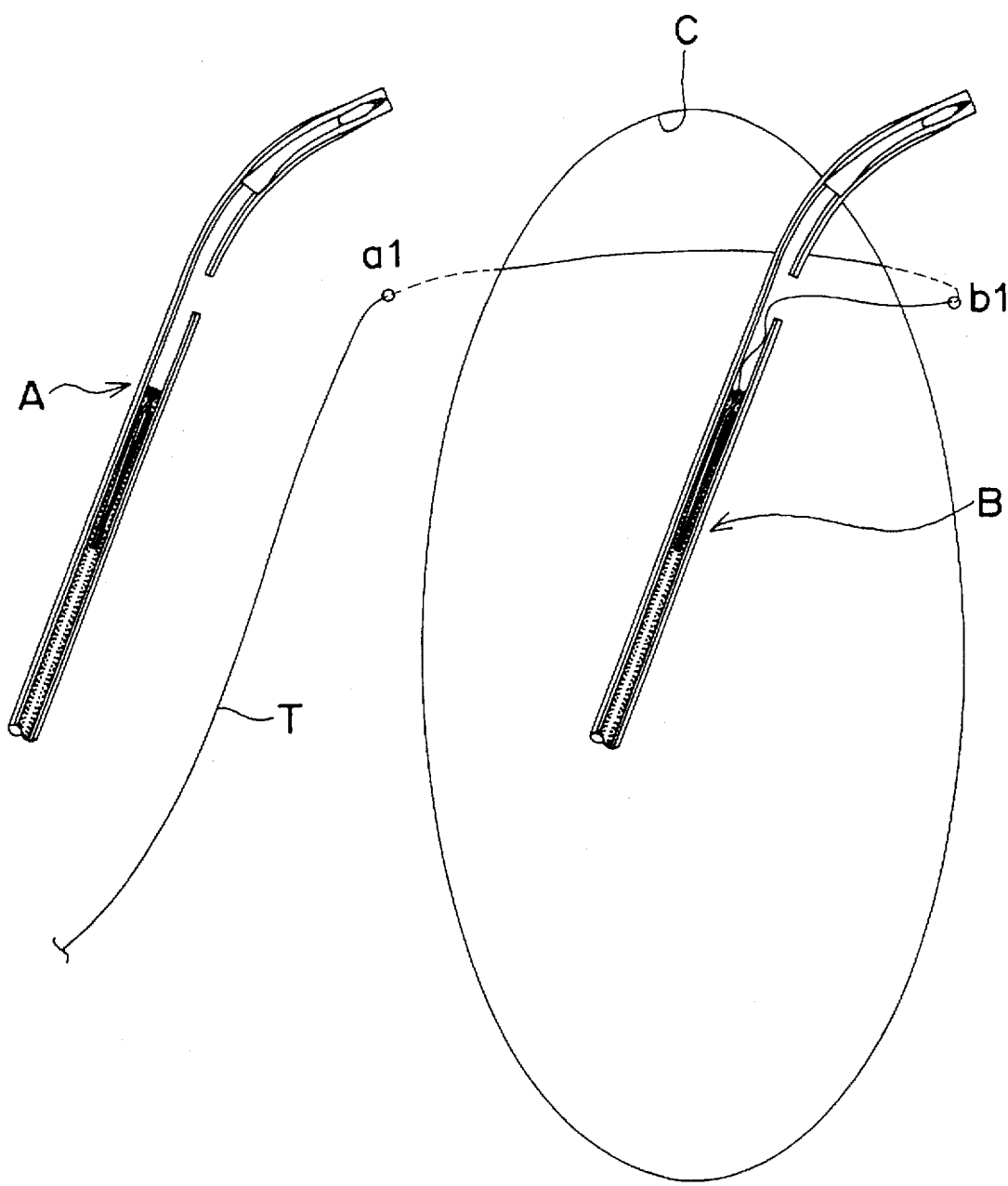

Both catheter assemblies "A" and "B" are restored to the initial state shown in FIG. 9 and then pulled back to the right atrium. Since suture "T" is held by catheter assembly "B", suture "T" is drawn into the right atrium by pulling back catheter assembly "B", whereby a stitch is put in the interatrial septum across the defect aperture "C", as shown in FIG. 13.

Figure 14:
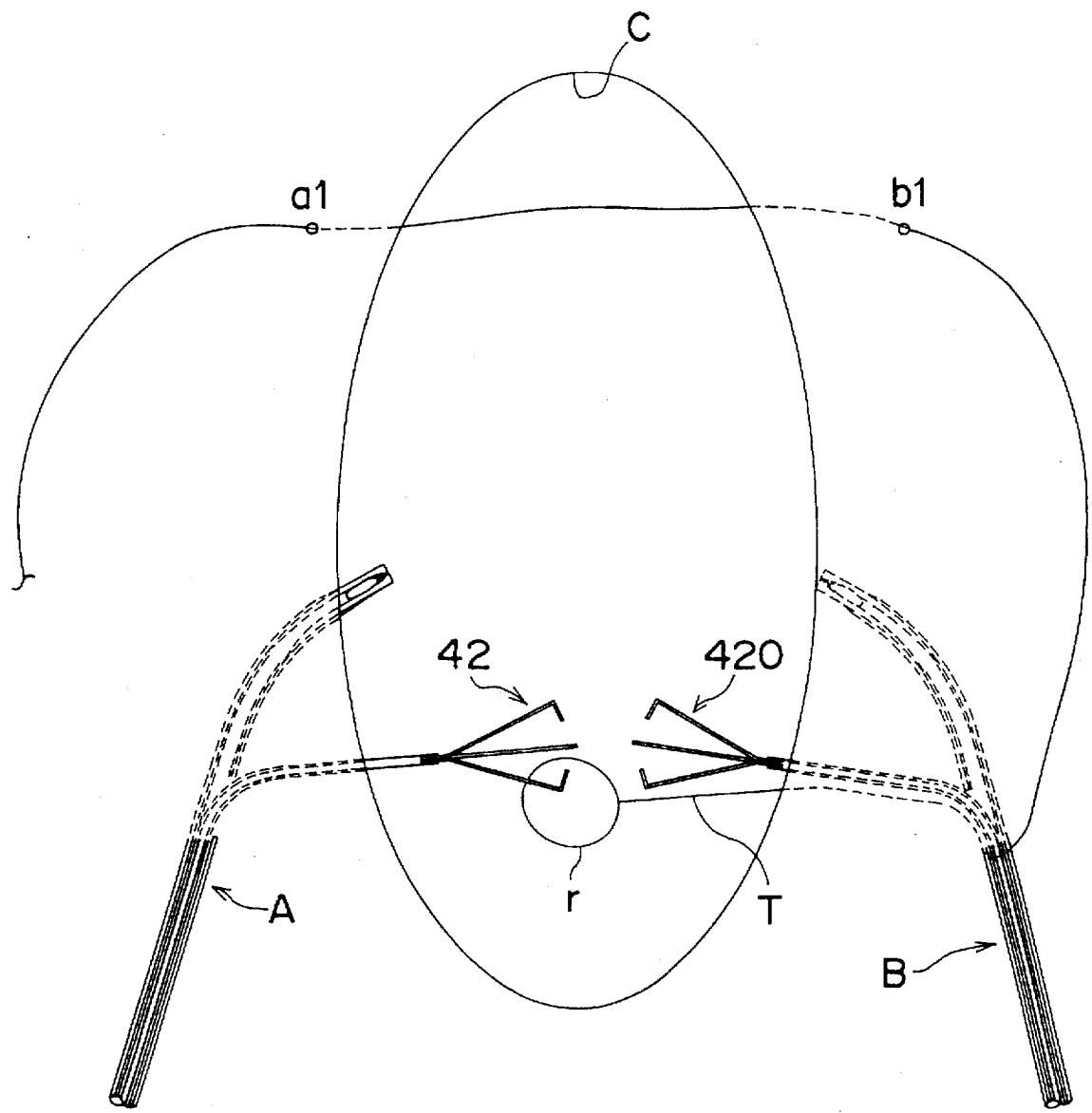
Figure 15:
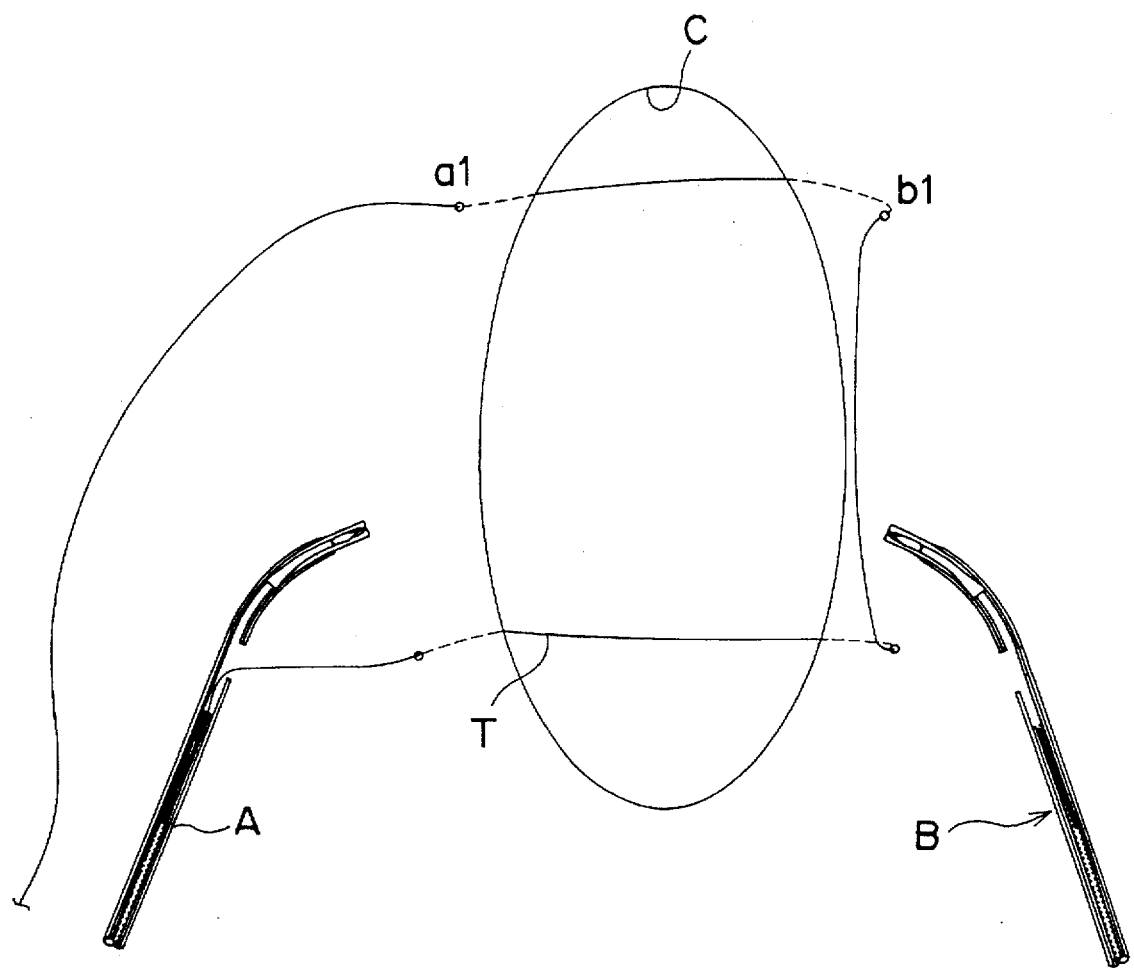

Then, piercing needle 280 of catheter assembly "B" with the suture is pierced into the next site "$b_2$" of the interatrial septum, which is spaced downward from the first pierced site "$b_1$" pierced by the catheter assembly "B", and introduced from the right atrium into the left atrium. Similarly, piercing needle 28 of catheter assembly "A" with no suture is pierced into the next site "$a_2$" of the interatrial septum spaced downward from the first site "$a_1$" and maneuvered into the left atrium to receive suture "T" from the suture-hooking means 420 of the catheter assembly "B" by the suture-hooking means 42, as shown in FIG. 14. Finally, both catheter assemblies "A" and "B" are restored to the initial state and then pulled back to the right atrium, whereby suture "T" is drawn into the right atrium by catheter assembly "B" and a second stitch is put in the interatrial septum across the defect aperture "C" in the form of a so-called mattress suture, as shown in FIG. 15.

Figure 17:
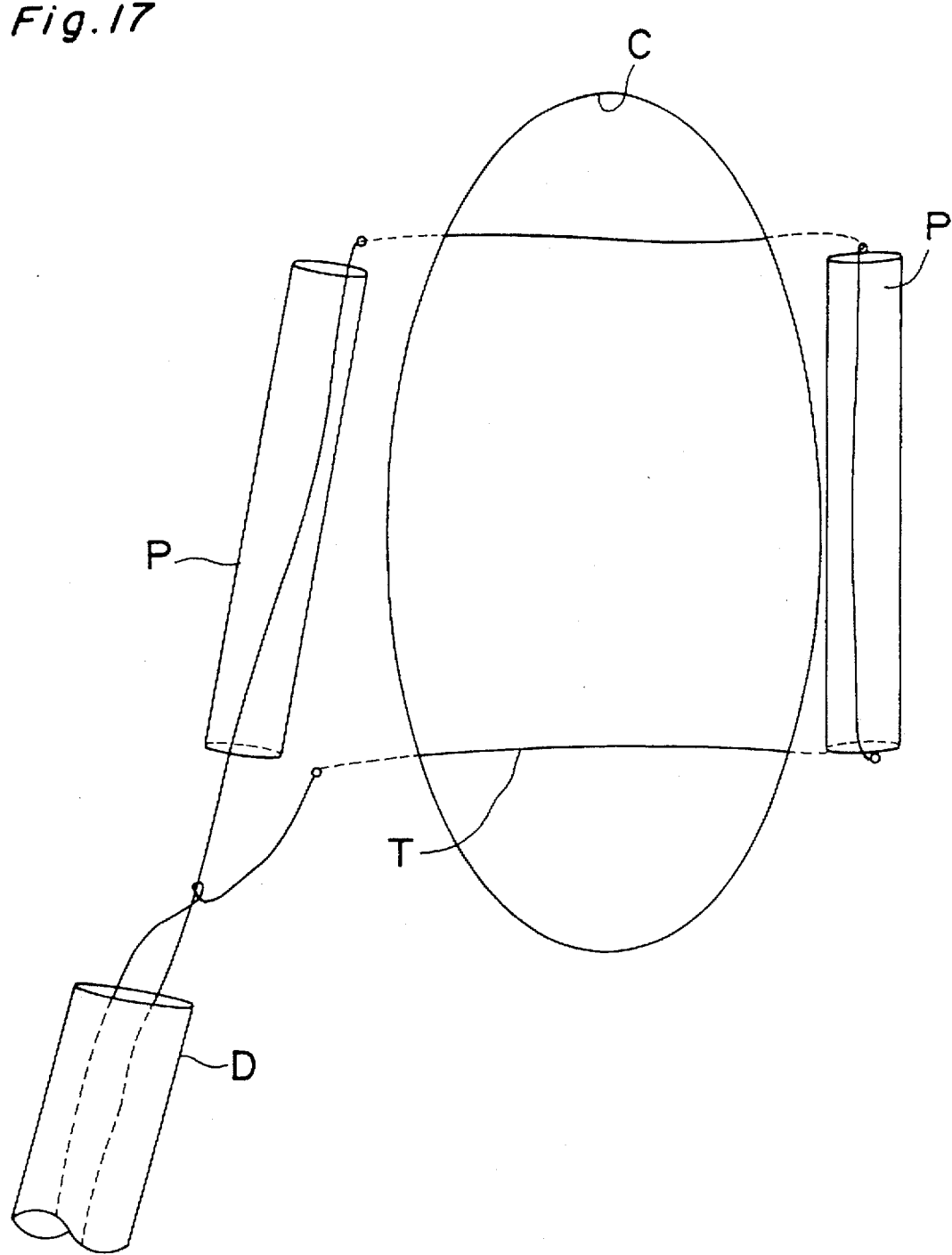

When pulling back catheter assembly "A" to the outside of the body, suture "T" is drawn to the outside of the body through the sheath "D", thus making it possible to make a knot "K" as shown in FIG. 16. If necessary, suture "T" may be provided with prejet "P" as shown in FIG. 17.

As mentioned above, use of the catheter assembly for intracardiac suture of the present invention makes it possible to close the diseased part by direct suture, so that it can be applied to any form of the atrial septal defect. Further, it is possible to close the atrial septal defect certainly. The intracardiac suture by the catheter assembly of the present invention is free from any danger since it does not leave any foreign material except the suture and since there is no separation or trouble of the devices which may occur in use of the conventional ASD devices.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

We claim:

1. A catheter assembly for intracardiac suture, comprising:

a hooking catheter bent at a distal portion thereof and provided at a distal end with having suture-hooking means and at the proximal end with a manipulating element;

a first sheath having a lumen for movably holding said hooking catheter therein, said first catheter being bent at a distal portion thereof at the same angle as the hooking catheter;

a piercing catheter having a lumen for movably holding said first sheath, said piercing catheter being provided at a distal end with a piercing needle and at the proximal end with a hemostatic means; and a second sheath having a lumen for movably holding said piercing catheter, said second sheath being provided with a hemostatic means at a proximal end thereof, said piercing catheter and second sheath being provided at each distal portion thereof with a side hole for extrusion of said first sheath so that said side hole of said piercing catheter is laid to lie the side hole of said second sheath to allow the first sheath to protrude therethrough when the piercing catheter is inserted into the second sheath until the tip of the piercing needle has reached to the tip of the second sheath.

2. The catheter assembly according to claim 1, wherein the piercing catheter and the second sheath are bent at a distal portion beyond the side hole at the same angle.

3. The catheter assembly according to claim 1, wherein said suture-hooking means is composed of two or more superelastic metal wires and formed into an L-shaped hook by bending the superelastic metal wires at the distal end thereof, and wherein said suture-hooking means being extended outwardly at the proximal portion and bent inwardly at the distal portion so that the distal portions do not intersect each other.

4. The catheter assembly according to claim 1, wherein the distal portion of the hooking means is bent at a bend angle within the range of 80 to 100 degrees.

5. The catheter assembly according to claim 1, wherein said piercing catheter and second sheath are provided at respective proximal ends with a side injection channel for injecting heparinized physiological saline into the suturing site.

* * * * *